United States Patent [19]

Itoh et al.

[11] Patent Number: 4,971,990

[45] Date of Patent: Nov. 20, 1990

[54] PHENOXYETHYLAMINE DERIVATIVES, FOR PREPARING THE SAME AND COMPOSITION FOR EXHIBITING EXCELLENT $\alpha_1$-BLOCKING ACTIVITY CONTAINING THE SAME

[75] Inventors: Yasuo Itoh, Katsuyamashi; Hideo Kato, Fukuishi; Eiichi Koshinaka; Nobuo Ogawa, both of Katsuyamashi; Kazuya Mitani, Fukuishi; Shunichiro Sakurai, Katsuyamashi, all of Japan

[73] Assignee: Hokuriku Pharmaceutical Co., Ltd., Katsuyamashi, Japan

[21] Appl. No.: 301,354

[22] Filed: Jan. 24, 1989

[30] Foreign Application Priority Data

Feb. 19, 1988 [JP] Japan .................................. 63-35063
Jun. 7, 1988 [JP] Japan ................................. 63-138345
Aug. 2, 1988 [JP] Japan ................................. 63-192162
Dec. 2, 1988 [JP] Japan ................................. 63-303897

[51] Int. Cl.⁵ .................. C07C 143/78; C07C 147/12; A61K 31/18; A61K 31/40; C07D 207/12
[52] U.S. Cl. .................................... 514/408; 514/601; 514/602; 514/603; 548/542; 564/84; 564/86; 564/90
[58] Field of Search ................. 548/542; 564/84, 86, 564/90; 514/408, 601, 602, 603

[56] References Cited

FOREIGN PATENT DOCUMENTS 110665 9/1981 Japan .
136561 8/1982 Japan .
114952 5/1987 Japan .
27471 2/1988 Japan .

OTHER PUBLICATIONS

J. Pharmacol. Exp. Ther. 239, 512 (1986).
J. Pharmacol. Exp. Ther. 236, 776 (1986).
J. Pharmacol. Exp. Ther. 235, 764 (1985).
J. Pharm. Pharmacol. 39, 316 (1987).
J. Pharm. Pharmacol. 36, 539 (1984).
Jpn. J. Pharmacol. 42, 579 (1986).
Jpn. J. Pharmacol. 41, 459 (1986).
Jpn. J. Pharmacol. 42, 237 (1986).
Naunyn–Schmiedeberg's Arch. Pharmacol. 328, 264 (1985).

*Primary Examiner*—David B. Springer
*Attorney, Agent, or Firm*—Gordon W. Hueschen

[57] ABSTRACT

Phenoxyethylamine derivatives represented by the general formula (I):

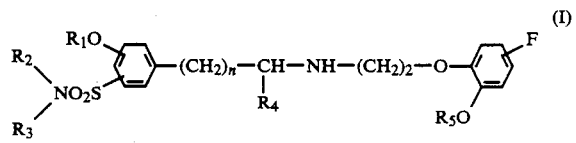

wherein $R_1$ and $R_5$ represent lower-alkyl, $R_2$ and $R_3$, which may be the same or different, each represents hydrogen or lower-alkyl, or

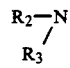

represents a 5- or 6-membered ring system which may include nitrogen, oxygen or sulfur as a ring membered atom, $R_4$ represents hydrogen or lower-alkyl, and n represents an integer selected from 1 to 3, their optical isomers and pharmacologically-acceptable acid addition salts, which exhibit excellent $\alpha_1$-blocking activity, a process for their preparation, pharmaceutical compositions thereof, and a method for the treatment of a subject afflicted with hypertension or dysuria by administrating such a compound, are all disclosed.

12 Claims, No Drawings

PHENOXYETHYLAMINE DERIVATIVES, FOR PREPARING THE SAME AND COMPOSITION FOR EXHIBITING EXCELLENT $\alpha_1$-BLOCKING ACTIVITY CONTAINING THE SAME

BACKGROUND OF THE INVENTION

1. Field of the Invention

The present invention relates to novel phenoxyethylamine derivatives represented by the following general formula (I), their optical isomers, pharmacologically-acceptable acid addition salts thereof, process for preparing the same, and pharmaceutical compositions exhibiting excellent $\alpha_1$-blocking activity containing the same as active ingredient which can be used in the treatment of hypertension or dysuria.

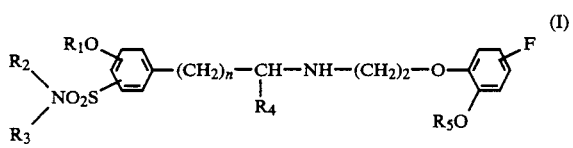

2. Description of the Prior Art

It is already known that an $\alpha_1$-blocker can be used for the treatment of hypertension and a number of $\alpha_1$-blockers have already been marketed or developed. Recently it was found that $\alpha_1$-blockers affect the smooth muscle of the lower urinary tract and a new use of the $\alpha_1$-blockers, namely, treatment of dysuria, hypertrophy of the prostatic gland and frequency of urination is being followed with interest. The compound YM-12617[Japan Kokai 56-110665], which is an example of compounds having a structure similar to those of the present invention, is also an $\alpha_1$-blocker. It has the formula;

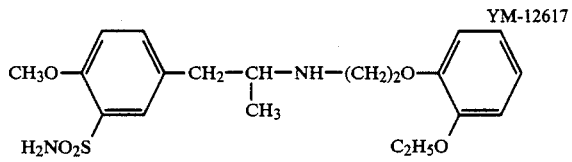

but medicaments such as YM-12617 are not satisfactory for practical use because of insufficient efficacy and the presence of side effects.

3. Summary of the Invention

As a result of extensive investigations, it has now been found that novel phenoxyethylamine derivatives represented by the general formula (I):

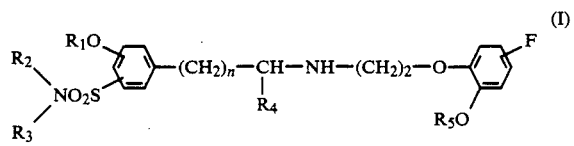

wherein $R_1$ and $R_5$ represent lower-alkyl, $R_2$ and $R_3$, which may be the same or different, each represents hydrogen or lower-alkyl, or

represents a 5- or 6-membered ring which may be substituted and may include a nitrogen, oxygen or sulfur atom as a ring membered atom, $R_4$ represents hydrogen or lower-alkyl and n represents an integer selected from 1 to 3, their optical isomers, and their pharmacologically-acceptable acid addition salts, exhibit excellent $\alpha_1$-blocking activity.

Further, according to the present invention, there are provided also a process for preparation of the novel phenoxyethylamine derivatives represented by the general formula (I), pharmaceutical compositions thereof, and a method of treating therewith.

DETAILED DESCRIPTION OF THE INVENTION

In this invention, the lower-alkyl moiety represented by $R_1$, $R_2$, $R_3$, $R_4$ and $R_5$ in the general formula (I) is, for example, methyl, ethyl, n-propyl, isopropyl, n-butyl, isobutyl, sec-butyl, tert-butyl and the like. The 5- or 6-membered ring represented by

is, for example, 1-pyrrolidinyl, 1-piperidinyl, 2-methyl-1-piperidinyl, 3-methyl-1-piperidinyl, 4-methyl-1-piperidinyl, 1-piperazinyl, 2-methyl-1-piperazinyl, 3-methyl-1-piperazinyl, 4-methyl-1-piperazinyl, 4-morpholinyl, 4-thiomorpholinyl, or the like. Typical examples of phenoxyethylamine derivatives embraced by the present invention are:

($\pm$)-5-[2-[2-(5-Fluoro-2-methoxyphenoxy)ethylamino]propyl]-2-methoxybenzenesulfonamide R-(−)-5-[2-[2-(5-Fluoro-2-methoxyphenoxy)ethylamino]propyl]-2-methoxybenzenesulfonamide S-(+)-5-[2-[2-(5-Fluoro-2-methoxyphenoxy)ethylamino]propyl]-2-methoxybenzenesulfonamide 5-[2-[2-(4-Fluoro-2-methoxyphenoxy)ethylamino]propyl]-2-methoxybenzenesulfonamide 5-[2-[2-(3-Fluoro-2-methoxyphenoxy)ethylamino]propyl]-2-methoxybenzenesulfonamide 1-[[5-[2-[2-(5-Fluoro-2-methoxyphenoxy)ethylamino]propyl]-2-methoxyphenyl]sulfonyl]pyrrolidine 1-[[5-[2-[2-(5-Fluoro-2-methoxyphenoxy)ethylamino]propyl]-2-methoxyphenyl]sulfonyl]piperidine 5-[2-[2-(2-Ethoxy-5-fluorophenoxy)ethylamino]propyl]-2-methoxybenzenesulfonamide 5-[2-[2-(5-Fluoro-2-methoxyphenoxy)ethylamino]propyl]-2-methoxy-N-methylbenzenesulfonamide N-Ethyl-5-[-2-[2-(5-fluoro-2-methoxyphenoxy)ethylamino]propyl]-2-methoxybenzenesulfonamide 5-[2-[2-(5-Fluoro-2-methoxyphenoxy)ethylamino]propyl]-2-methoxy-N-n-propylbenzenesulfonamide N-n-Butyl-5-[2-[2-(5-fluoro-2-methoxyphenoxy)ethylamino]propyl]-2-methoxybenzenesulfonamide 1-[[5-[2-[2-(5-Fluoro-2-methoxyphenoxy)ethylamino]propyl]-2-methoxyphenyl]sulfonyl]-4-methylpiperazine N-[[5-[2-[2-(5-Fluoro-2-methoxyphenoxy)ethylamino]propyl]-2-methoxyphenyl]sulfonyl]morpholine N-[[5-[2-2-(5-Fluoro-2-methoxyphenoxy)ethylamino]-
propyl]-2-methoxyphenyl]sulfonyl]thiomorpholine 5-[2-[2-(5-Fluoro-2-methoxyphenoxy)ethylamino]-
propyl]-2-methoxy-N,N-dimethylbenzenesulfonamide 5-[2-[2-(5-Fluoro-2-ethoxyphenoxy)ethylamino]-
propyl]-2-methoxy-N,N-dimethylbenzenesulfonamide N,N-Diethyl-5-[2-[2-(5-fluoro-2-methoxyphenoxy)ethylamino]-propyl]-2-methoxybenzenesulfonamide 3-[2-[2-(5-Fluoro-2-methoxyphenoxy)ethylamino]-
propyl]-4-methoxybenzenesulfonamide 2-Ethoxy-5-[2-[2-(5-fluoro-2-methoxyphenoxy)ethylamino]propyl]-benzenesulfonamide 2-Ethoxy-5-[2-[2-(4-fluoro-2-methoxyphenoxy)ethylamino]propyl]-benzenesulfonamide 2-Ethoxy-5-[2-[2-(2-ethoxy-5-fluorophenoxy)ethylamino]propyl]-benzenesulfonamide 2-Ethoxy-5-[2-[2-(5-fluoro-2-methoxyphenoxy)ethylamino]propyl]-N-methylbenzenesulfonamide 2-Ethoxy-5-[2-[2-(5-fluoro-2-methoxyphenoxy)ethylamino]propyl]-N,N-dimethylbenzenesulfonamide 5-[2-[2-(5-Fluoro-2-methoxyphenoxy)ethylamino]-
propyl]-2-n-propoxybenzenesulfonamide 2-n-Butoxy-5-[2-[2-(5-fluoro-2-methoxyphenoxy)ethylamino]-propyl]benzenesulfonamide 5-[2-[2-(5-Fluoro-2-n-propoxyphenoxy)ethylamino]-
propyl]-2-methoxybenzenesulfonamide 5-[2-[2-(2-n-Butoxy-5-fluorophenoxy)ethylamino]-
propyl]-2-methoxybenzenesulfonamide 5-[3-[2-(5-Fluoro-2-methoxyphenoxy)ethylamino]pentyl]-2-methoxybenzenesulfonamide 5-[3-[2(5-Fluoro-2-methoxyphenoxy)ethylamino]butyl]-2-methoxybenzenesulfonamide 5-[2-[2-(5-Fluoro-2-methoxyphenoxy)ethylamino]-
butyl]-2-methoxybenzenesulfonamide 5-[4-[2-(5-Fluoro-2-methoxyphenoxy)ethylamino]pentyl]-2-methoxybenzenesulfonamide 5-[2-[2-(5-Fluoro-2-methoxyphenoxy)ethylamino]ethyl]-2-methoxybenzenesulfonamide 5-[3-[2-(5-Fluoro-2-methoxyphenoxy)ethylamino]-
propyl]-2-methoxybenzenesulfonamide 5-[4-[2-(5-Fluoro-2-methoxyphenoxy)ethylamino]-
butyl]-2-methoxybenzenesulfonamide 5-[2-[2-(5Fluoro-2-n-propoxyphenoxy)ethylamino]-
propyl]-2-methoxy-N,N-dimethylbenzenesulfonamide N-n-Butyl-5-[2-[2-(5-fluoro-2-methoxyphenoxy)ethylamino]propyl]-2-methoxy-N-methylbenzenesulfonamide 5-[2-[2-(2-Ethoxy-4-fluorophenoxy)ethylamino]butyl]-2-n-propoxybenzenesulfonamide 5-[2-[2-(2-Ethoxy-3-fluorophenoxy)ethylamino]-
propyl]-2-n-propoxybenzenesulfonamide 5-[3-[2-(5-Fluoro-2-n-propoxyphenoxy)ethylamino]-
propyl]-2-methoxy-N,N-dimethylbenzenesulfonamide N-n-Butyl-5-[2-[2-(4-fluoro-2-methoxyphenoxy)ethylamino]ethyl]-2-methoxy-N-methylbenzenesulfonamide 1-[[5-[2-[2-(2-Ethoxy-4-fluorophenoxy)ethylamino]-
propyl]-2-methoxyphenyl]sulfonyl]pyrrolidine 1-[[5-[2-[2-(2-n-Butoxy-4-fluorophenoxy)ethylamino]-
propyl]-2-methoxyphenyl]sulfonyl]piperidine 5-[2-[2-(5-Fluoro-2-n-propoxyphenoxy)ethylamino]-
propyl]-2-methoxy-N-methylbenzenesulfonamide N-Ethoxy-5-[2-[2-(2-ethoxy-4-fluorophenoxy)ethylamino]propyl]-2-methoxybenzenesulfonamide Pharmacologically-acceptable acid addition salts of the compounds represented by the general formula (I) include, for example, mineral acid salts such as the hydrochloride, hydrobromide, hydroiodide, nitrate, sulfate, phosphate, metaphosphate, and the like, and organic acid salts such as the acetate, maleate, fumarate, citrate, oxalate, succinate, malate, tartarate, lactate, malonate, propionate, mandelate, p-toluenesulfonate, methanesulfonate, DL-10-camphorsulfonate, gluconate, and the like.

Among the compounds represented by the general formula (I), compounds with an asymmetric carbon atom are included. These compounds can take optically active forms. Therefore, all of the racemates and the R- and S-optical isomers are included in this invention.

According to the present invention, the novel phenoxyethylamine derivatives represented by the general formula (I) can be prepared by various methods.

In the first method, the compounds represented by the said formula (I) can be prepared by reacting phenoxyethylamines represented by the general formula (II), $$H_2N-(CH_2)_2-O-\underset{R_5O}{\underset{|}{\text{C}_6H_3}}-F \quad (II)$$

wherein $R_5$ has the same meaning as that described above, with carbonyl compounds represented by the general formula (III), $$\underset{R_3}{\underset{R_2}{\overset{R_1O}{\text{C}_6H_2(NO_2S)}}}-(CH_2)_n-\overset{O}{\underset{\|}{C}}-R_4 \quad (III)$$

wherein $R_1$, $R_2$, $R_3$, $R_4$ and n have the same meaning as that described above in the presence of a solvent, and then hydrogenating or treating with a reducing agent.

The solvent used in the process can be any kind of solvents which does not inhibit the reaction. Examples of the solvent which may be used are methanol, ethanol, n-butanol, ether, tetrahydrofuran and the like.

As reducing agent in the present reaction can be used, for example, sodium borohydride, sodium cyanoborohydride, lithium aluminum hydride, and the like. The hydrogenation is to be carried out under atmospheric or higher pressure. As the catalyst can be used, for example, palladium-carbon, platinum oxide, Raney nickel, and the like.

The above-mentioned reaction is to be carried out at a temperature within the range of room temperature to the reflux temperature of the reaction solvent used.

The phenoxyethylamines with a fluorine atom represented by the said formula (II) are novel compounds and are important intermediates for the preparation of the compounds represented by the said formula (I). The compounds (II) can be prepared by a process illustrated in the following scheme:

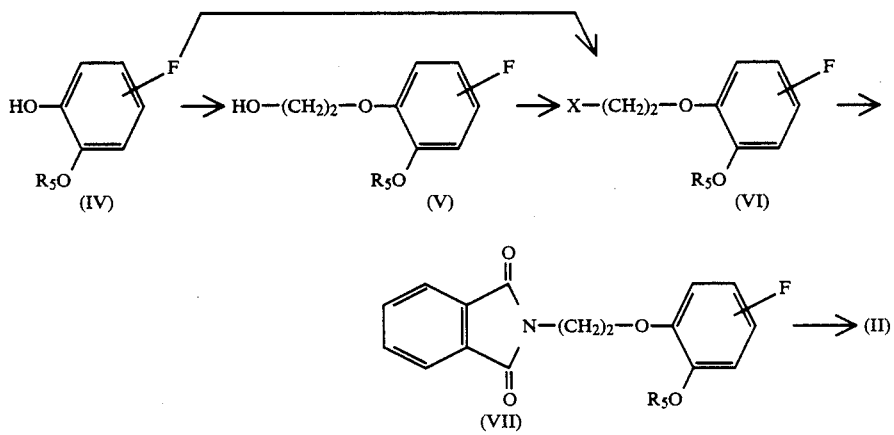

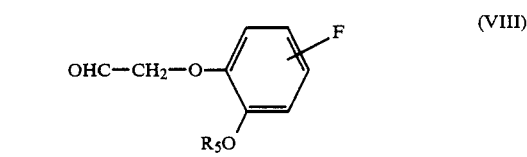

wherein $R_5$ has the same meaning as that described above, with amine derivatives represented by the general formula (IX),

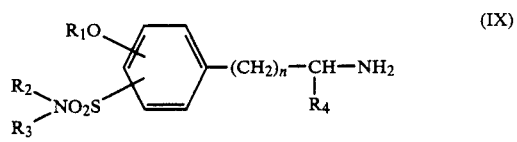

wherein $R_1$, $R_2$, $R_3$, $R_4$ and n have the same meaning as that described above or these optically active amines, in the presence of a solvent, and then hydrogenating or treating with a reducing agent.

The solvent used in the process can be any kind of solvent which does not inhibit the reaction. Examples of the solvent which may be used are methanol, ethanol, n-butanol, ether, tetrahydrofuran and the like. As reducing agent in the present reaction can be used, for example, sodium borohydride, sodium cyanoborohydride, lithium aluminum hydride, and the like. The hydrogenation is to be carried out under atmospheric or higher pressure. As the catalyst can be used, for example, palladium-carbon, platinum oxide, Raney nickel, and the like. The above mentioned reaction is to be carried out at a temperature within the range of room temperature to the reflux temperature of the reaction solvent used. The phenoxyacetaldehydes with a fluorine atom represented by the said formula (VIII) are novel compounds and are important intermediates for the preparation of the compounds represented by the said formula (I). The compounds (VIII) can be prepared by a process illustrated by the following scheme:

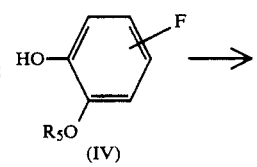

wherein X represents a halogen and $R_5$ has the same meaning as that described above. That is, the compounds (IV) are reacted with an ethylene halide or ethylene chlorohalide in an organic solvent (dimethyl sulfoxide, N,N-dimethylformamide, toluene, etc.) in the presence of a base (pyridine, triethylamine, potassium carbonate, sodium carbonate, etc.) to give the compounds (VI), or the compounds (IV) are reacted with ethylene carbonate or ethylene chlorohydrin in an organic solvent (dimethyl sulfoxide, N,N-dimethylformamide, toluene, etc.) in the presence of a base (potassium carbonate, sodium carbonate, sodium hydroxide, etc.) to give the compounds (V) and then V are treated with an agent for halogenation (thionyl chloride, phosphorus oxychloride, phosphorus pentachloride, thionyl bromide, triphenylphosphine dibromide, etc.) either in the presence or absence of an organic solvent (chloroform, benzene, toluene, etc.) to give the compounds (VI).

The compounds (VI) are reacted with phthalimide in an organic solvent (N,N-dimethylformamide, dimethyl sulfoxide, toluene, etc.) in the presence of a base (potassium carbonate, sodium carbonate, etc.) to give the compounds (VII), and then VII are hydrolyzed with aq. alkali (sodium hydroxide, potassium hydroxide, etc.) or treated with hydrazine in an organic solvent (methanol, ethanol, etc.) to give the desired compounds (II). All of the above-mentioned reactions are to be carried out at a temperature within the range of room temperature to the reflux temperature of the reaction solvent used.

The carbonyl compounds represented by the said formula (III), most of which are novel compounds, can be prepared by a process illustrated by the following scheme and the details of the preparation are shown in the References.

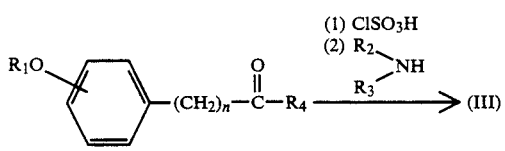

wherein $R_1$, $R_2$, $R_3$, $R_4$ and n have the same meaning as that described above.

In the second method, the compounds represented by the said formula (I) can be prepared by reacting phenoxyacetaldehydes represented by the general formula (VIII),

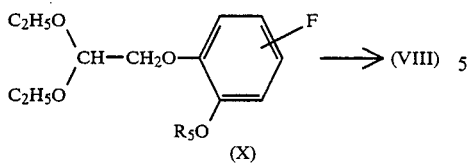

wherein $R_5$ has the same meaning as that described above.

That is, the compounds (IV) are reacted with chloroacetaldehyde diethylacetal in an organic solvent (tetrahydrofuran, N,N-dimethylformamide, dimethylsulfoxide, etc.) in the presence of a base (potassium carbonate, sodium carbonate, triethylamine, sodium hydride, sodium amide, etc.) to give the compounds (X). In this reaction potassium iodide or sodium iodide may be added. The obtained compounds (X) are hydrolyzed with an organic acid (oxalic acid, maleic acid, etc.) or a mineral acid (sulfuric acid, hydrochloric acid, etc.) in an organic solvent (acetone, tetrahydrofuran, etc.) or an aqueous organic solvent to give the phenoxyacetaldehydes (VIII). All of the above-mentioned reactions are to be carried out at a temperature within the range of room temperature to the reflux temperature of the reaction solvent used. The amine compounds represented by the said formula (IX) and these optically active amines, most of which are novel compounds, can be prepared by a process illustrated by the following scheme and the details of the preparation are shown in the References.

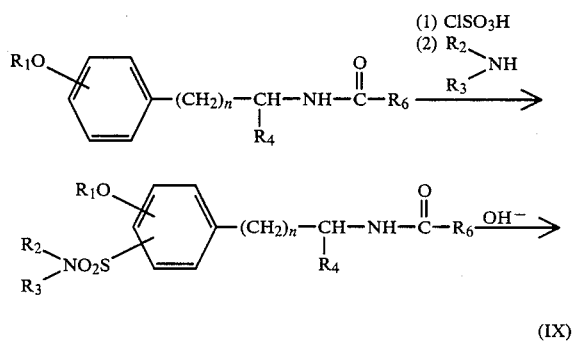

wherein $R_1$, $R_2$, $R_3$, $R_4$ and n have the same meaning as that described above and $R_6$ represents lower alkyl or lower halogenoalkyl.

In the third method, the compounds represented by the said formula (I) can be prepared by reacting fluorophenoxyalkane derivatives represented by the said formula (VI) with amine derivatives represented by the said formula (IX) in no solvent or an organic solvent, if necessary, in the presence of a base and potassium iodide or sodium iodide. The solvent used in the process can be any kind of solvents which does not inhibit the reaction. Examples of the solvent which may be used are methanol, ethanol, isopropanol, n-butanol, dimethylsulfoxide, N,N-dimethylformamide, benzene, toluene, tetrahydrofuran, and the like. As the base in the present reaction can be used, for example, pyridine, triethylamine, potassium carbonate, sodium carbonate, and the like. The reaction is to be carried out at a temperature within the range of room temperature to 200° C. In the fourth method, the optically active compounds represented by the said formula (I) can be prepared by producing a salt of the racemates with a optical resolving agent and then recrystallizing the obtained salt. As the optical resolving agent in the present reaction can be used, for example, D-10-camphorsulfonic acid, L-10-camphorsulfonic acid, (+)-dibenzoyl-D-tartaric acid, (−)-dibenzoyl-L-tartaric acid, L-(+)-tartaric acid, D-(−)-tartaric acid, L-(+)-mandelic acid, D-(−)-mandelic acid, D-camphorcarboxylic acid, D-malic acid, L-malic acid, (+)-di-p-toluoyl-D-tartaric acid, (−)-di-p-toluoyl-L-tartaric acid, (−) menthyloxyacetic acid, (−)-diacetyl-L-tartaric acid, (+)-monomethyl-D-tartaric acid, (−)-monomethyl-L-tartaric acid, (−)-diacetone-2-ketogulonic acid, (−)-quinic acid, D-glutamic acid, L-glutamic acid, (s)-(−)-pyrrolidone-5-carboxylic acid, (R)-(−)-2-phenylpropionic acid, (S)-(+)-2-phenylpropionic acid, (S)-1-(2-naphthylsulfonyl)pyrrolidine-2-carboxylic acid, (S)-1-(4-toluenesulfonyl)pyrrolidine-2-carboxylic acid, and the like.

As the solvent used for the optical resolution can be used, for example, water, lower alcohols such as methanol, ethanol, and isopropanol, halogenohydrocarbons, such as chloroform, dichloromethane, dichloroethane and carbon tetrachloride, ketones such as acetone and methylethyl ketone, ethers such as diethyl ether, diisopropyl ether and dioxane, aromatic hydrocarbons such as benzene, toluene and xylene, hydrocarbons such as hexane, pentane and cyclohexane, nitriles such as acetonitrile, esters such as ethyl acetate and ethyl formate, amides such as N,N-dimethylformamide and N,N-dimethylacetamide, aprotic organic solvents such as dimethylsulfoxide and nitromethane, and a mixture of solvents described above.

The optical resolution is to be carried out at a temperature that is from cooling with ice-water to heating.

A compound of the present invention represented by general formula (I) can be administrated per os, e.g., in the form of pills or tablets, in which it may be present together with any of the usual pharmaceutical carriers, conventionally by compounding a compound of this invention together with a customary carrier or adjuvant, such as talc, magnesium stearate, starch, lactose, gelatin, any of numerous gums, or the like. Thus, in their most advantageous form, the compositions of this invention will contain a non-toxic pharmaceutical carrier in addition to the active ingredient of the present invention. Exemplary solid carriers are lactose, magnesium stearate, calcium stearate, starch, terra alba, dicalcium acacia, or the like.

Representative liquid carriers are peanut oil, sesame oil, olive oil, water, or the like. The active agents of this invention can be conveniently administered in such compositions containing active ingredient so as to eventually be within the dosage range illustrated hereinafter. Thus, a wide variety of pharmaceutical forms suitable for many modes of administration and dosages may be employed. For oral administration, the active ingredient and pharmaceutical carrier may, for example, take the form of a powder, granule, pill, tablet, capsule, lozenge, elixir, syrup, or other liquid suspension or emulsion whereas, for parenteral administration, the composition may be in the form of a sterile solution. For intra rectal administration, the composition may be in the form of a suppository.

The method of using the compounds of this invention comprises internally or externally administering a compound of this invention, preferably orally or parenterally and preferably admixed with the pharmaceutical carrier, for example, in the form of any of the above compositions, or filled into a capsule, to alleviate conditions to be treated and symptoms thereof in a living animal body. Illustratively, it may be used in an amount of about 0.01 to about 100 mg per day (divided into three parts), preferably in amount of 0.02 to 50 mg per day (divided into three parts) for oral dose, while parenteral dosages are usually less and ordinarily about one-half of the oral dose. The unit dose is preferably given a suitable number of times daily, typically three times.

The unit dose may vary depending upon the number of times given. Naturally, a suitable clinical dose must be adjusted in accordance with the condition, age, and weight of the patient, and it goes without saying that the enhanced activities of the compounds of the invention, together with their reduced side effects, also make them suitable for wide variations, and this invention therefore should not be limited by the exact ranges stated. The exact dosage, both unit dosage and daily dosage, will of course have to be determined according to established medical principles.

The following experiments show the excellent effect of the present compounds (compound number means Example compound number), for example, $\alpha_1$-adrenoceptor blocking action and dopamine $D_2$-receptor radioligand binding assay, while using 5-[2-[[2-(2-ethoxyphenoxy)ethyl]amino]propyl]-2-methoxybenzene-sulfonamide hydrochloride : YM-12617 as reference compound.

There are possibilities that compounds which have affinities to dopamine $D_2$-receptors produce clinical side effects such as nausea, vomiting or abnormal prolactin secretion. Therefore, the compound which selectively acts as an $\alpha_1$-adrenoceptor is most useful.

EXPERIMENT 1

$\alpha_1$-adrenoceptor blocking action

Method: The thoracic aorta were isolated from male rabbits (Japanese white, about 2.5 kg b.w.) and helically cut. The preparations were suspended in Krebs-Henseleit solution maintained at 37° C. and aerated with a gas mixture of 95%$O_2$+5%$CO_2$. Responses to drugs were recorded isometrically under a tension of 2 g. After an equilibration period of about 60 min., cumulative concentration-response curves for noradrenaline were constructed. The preparations were exposed to the test compounds for 30 min. before rechallenge with noradrenaline. The dose ratio was obtained from the ratio of an $ED_{50}$ value (the concentration needs to produce the half maximum response) of noradrenaline in the presence and absence of the test compound. The test compounds dissociation constants ($K_B$) were determined according to the following equation.

$$K_B = [\text{concentration of the test compound (M)}/(\text{dose ratio} - 1)]$$

The $pA_2$ values were then expressed as the negative logarithm of $K_B$.

This value represents the blocking activity of a test compound to $\alpha_1$-adrenoceptors. In these experimental periods, $10^{-6}$M propranolol was treated to block $\beta$-adrenoceptors. The results shown in Table 1-a indicate that the $\alpha_1$-adrenoceptor blocking activites of the test compounds are almost the as same as that of YM-12617.

EXPERIMENT 2

Dopamine $D_2$-receptor radioligand-binding assay

Method: These experiments were done according to the method of Coward, D et al. (Naunyn-Schmiedeberg's Archives of Pharmacology (1987)335, 115-122). Briefly, brain striatum were isolated from male Wistar rats (about 200 g b.w.). The tissues were homogenaized in ice-cold 50 mM Tris buffer (pH7.4) with a polytron and centrifuged at 50,000 g for 15 min.. The pellets were homogenaized in the same Tris buffer and incubated for 5 min. at 37° C. The homogenates were centrifuged and synaptic membrane fractions were obtained. The membrane fractions were incubated with $^3$H-spiperone and various concentrations of the test compounds for 50 min. at 25° C. The reaction was terminated by filtration on a GF/B glass filter under vacuum. The radioactivity on the filter was measured using a liquid scintillation counter. The test compounds' dissociation constants ($K_i$) were determined according to the following equation.

$$K_i = IC_{50}/[1 + (L/K_d)]$$

$IC_{50}$ : the test compound concentration needed to inhibit 50% of $^3$H-spiperone binding calculated by pseudo-Hill plot.

L : $^3$H-spiperone concentration $K_d$ : $^3$H-spiperone dissociation constant calculated by Scatchard plot.

The $pK_i$ values was then expressed as the negative logarithum of $K_i$. This value represents an affinity of the test compound to dopamine $D_2$-receptors. Non-specific binding of $^3$H-spiperone was determined in the presence of $10^{-5}$M sulpiride. Protein concentration was determined by the method of Lowry. The results showed in Table 1-b indicate that the affinities of the test compounds to dopamine $D_2$-receptors were lower than that of YM-12617.

TABLE 1

| test Compound | 1-a $pA_2$ value | 1-b $pK_i$ value |
|---|---|---|
| Example 1 (as HCl salt) | 9.45 | 6.92 |
| Example 2 | 9.05 | 6.78 |
| Example 5 | 8.98 | 7.08 |
| Example 9 | 9.34 | 7.03 |
| Example 10 | 9.42 | 6.96 |
| Example 11 | 9.33 | 7.19 |
| Example 12 | 9.10 | 7.05 |
| Example 14 | 9.69 | 7.63 |
| Example 15 | 9.48 | 7.59 |
| Example 20 | 9.10 | 6.89 |
| Example 21 | 9.14 | 7.03 |
| Example 22 | 9.08 | 7.11 |
| Example 34 (as HCl salt) | 9.77 | 7.13 |
| YM-12617 | 9.38 | 7.68 |

The selectivity of the test compound to $\alpha_1$-adrenoceptors compared to dopamine $D_2$-receptors is determined according to the following equation.

$$\alpha_1\text{-adrenoceptor selectivity} = 10^{(pA_2 - pK_i)}$$

The results shown in Table 2 indicate that the selectivities of the test compounds to $\alpha_1$-adrenoceptors are superior to that of YM-12617.

TABLE 2

| test compound | α₁-adrenoceptor selectivity $10^{(pA2-pKi)}$ |
| --- | --- |
| Example 1 (as HCl salt) | 339 |
| Example 2 | 186 |
| Example 5 | 79 |
| Example 10 | 288 |
| Example 14 | 115 |
| Example 15 | 78 |
| Example 34 (as HCl salt) | 437 |
| YM-12617 | 50 |

The following References and Examples are given by way of illustration only and all not to be construed as limiting.

REFERENCE 1

2-(2-Bromoethoxy)-4-fluoroanisole

A suspension of 10.0 g of 5-fluoro-2-methoxyphenol, 52.9 g of ethylenebromide and 14.6 g of potassium carbonate in 50 ml of N,N-dimethylformamide was heated for 11 hours at 80° C. After cooling, the reaction mixture was poured into water and extracted with ethyl acetate. The extract was washed with water, dried and evaporated. The residue was chromatographed on silica gel using 50% chloroform-n-hexane as an eluent to give 11.6 g of the desired compound as a colorless oil.

Mass spectrum: m/z: 248,250(1:1,M+).

NMR spectrum: δ(CDCl₃) ppm: 3.65(2H,t-d, J=6.5Hz, 0.5Hz), 3.84(3H,s), 4.30(2H,t-d, J=6.5,0.5Hz), 6.48–6.96(3H,m).

REFERENCE 2

1-(4-Propoxyphenyl)-2-propanone

A suspension of 15.0 g of 1-(4-hydroxyphenyl)-2-propanone, 24.6 g of 1-bromopropane and 13.8 g of potassium carbonate in 100 ml of N,N-dimethylformamide was heated for 4 hours at 65°–70° C. After cooling, the reaction mixture was poured into water and extracted with ether. The extract was washed with water, dried and evaporated. The residue was distilled to give 15.2 g of the desired compound as a pale yellow oil, b.p.136°–138° C. (7 mmHg).

NMR spectrum δ (CDCl₃)ppm: 1.03(3,t,J=7.5 Hz), 1.56–2.04(2H,m), 2.13(3H,s), 3.90(2H,t,J=6.5 Hz), 6.85(2H,d,J=9 Hz), 7.10(2H,d,J=9 Hz).

High resolution mass spectrum for $C_{12}H_{16}O_2$: Calculated m/z : 192.1150. Found m/z : 192.1127.

REFERENCE 3

2-Methoxy-5-(2-oxopropyl)benzenesulfonamide

To 125 g of chlorosulfonic acid were added dropwise 25.0 g of 4-methoxyphenylacetone with stirring under ice cooling. The reaction mixture was stirred for 2 hours at room temperature, poured into ice water and extracted with ethyl acetate. The extract was washed with water, dried and evaporated to give 19.0 g of brown crystals. To a solution of the obtained crystals in 200 ml of tetrahydrofuran were added dropwise 25 ml of ammonia water with stirring under ice cooling and then the reaction mixture was stirred for 2 hours at room temperature. The solvent was removed and washed with water to give 13.0 g of the desired compound as pale brown crystals which were recrystallized from methanol as pale brown prisms, m.p.194°–196° C.

Analysis for $C_{10}H_{13}NO_4S$ : Calculated %: C, 49.37; H, 5.39; N, 5.76. Found %: C, 49.32; H, 5.44; N, 5.63.

In the same manner as described in Reference 3, the compounds of References 4 to 21 were prepared.

REFERENCE 4

1-[[2-Methoxy-5-(2-oxopropyl)phenyl] sulfonyl] pyrrolidine

Pale yellowish brown needles, m.p. 104°–105° C. (iso-PrOH). Analysis for $C_{14}H_{19}NO_4S$ : Calculated %: C, 56.55; H, 6.44; N, 4.71. Found %: C, 56.29; H, 6.48; N, 4.59.

REFERENCE 5

1-[[2-Methoxy-5-(2-oxopropyl)phenyl] sulfonyl] piperidine

Pale yellowish brown prisms, m.p. 103°–105° C. (iso-PrOH).

Analysis for $C_{15}H_{21}NO_4S$ : Calculated %: C, 57.86; H, 6.80; N, 4.50. Found %: C, 57.74; H, 6.51; N, 4.36.

REFERENCE 6

1-[[2-Methoxy-5-(2-oxopropyl)phenyl] sulfonyl] -4-methyl-piperazine

Pale yellow crystals, m.p. 108°–109° C. (iso-PrOH).

Analysis for $C_{15}H_{22}N_2O_4S$: Calculated %: C, 55.19; H, 6.79; N, 8.58. Found %: C, 55.13; H, 6.86; N, 8.48.

REFERENCE 7

N-[[2-Methoxy-5-(2-oxopropyl)phenyl] sulfonyl] morpholine

Pale yellow oil.

NMR spectrum: δ (CDCl₃)ppm: 2.19(3H,s) 3.12–3.40(4H,m), 3.61–3.88(4H,m), 3.71(2H,s),3.92(3H,s), 7.00(1H,d,J=8.5Hz), 7.37(1H,d—d,J =8.5,2 Hz), 7.69(1H,d,J=2 Hz).

High resolution mass spectrum for $C_{14}H_{19}NO_5S$: Calculated m/z: 313.0984. Found m/z: 313.0987.

REFERENCE 8

2-Methoxy-5-(4-oxopentyl)benzenesulfonamide

Colorless needles, m.p. 115°–116° C. (EtOH).

Analysis for $C_{12}H_{17}NO_4S$: Calculated %: C, 53.12; H, 6.32; N, 5.16. Found %: C, 52.96; H, 6.18; N, 5.01.

REFERENCE 9

5-(2-Oxopropyl)-2-propoxybenzenesulfonamide

Colorless prisms, m.p. 105.5°–107° C. (EtOH).

Analysis for $C_{12}H_{17}NO_4S$: Calculated %: C, 53.12; H, 6.32; N, 5.16. Found %: C, 53.01; H, 6.51; N, 5.15.

REFERENCE 10

2-Butoxy-5-(2-oxopropyl)benzenesulfonamide

Colorless crystals, m.p. 107°–109° C. (AcOEt-iso-Pr₂O).

Analysis for $C_{13}H_{19}NO_4S$: Calculated %: C, 54.72; H, 6.71; N, 4.91. Found %: C, 54.58; H, 6.52; N, 4.84.

REFERENCE 11

2-Ethoxy-5-(2-oxopropyl)benzenesulfonamide

Pale yellow crystals, m.p. 158°–159° C. (MeOH).

Analysis for $C_{11}H_{15}NO_4S$: Calculated %: C, 51.35; H, 5.88; N, 5.44. Found %: C, 51.41; H, 5.97; N, 5.54.

REFERENCE 12

2-Ethoxy-N-methyl-5-(2-oxopropyl)benzenesulfonamide

Pale yellow crystals, m.p. 91°–93° C. (iso-PrOH-Et$_2$O).

Analysis for C$_{12}$H$_{17}$NO$_4$S: Calculated %: C, 53.12; H, 6.32; N, 5.16. Found %: C, 52.79; H, 6.32; N, 5.05.

REFERENCE 13

2-Ethoxy-N,N-dimethyl-5-(2-oxopropyl)benzenesulfonamide

Pale yellow crystals, m.p. 78°–80° C. (iso-PrOH-Et$_2$O).

Analysis for C$_{13}$H$_{19}$NO$_4$S: Calculated %: C, 54.72; H, 6.71; N, 4.91. Found %: C, 54.49; H, 6.80; N, 4.78.

REFERENCE 14

2-Methoxy-5-(3-oxobutyl)benzenesulfonamide

Colorless scales, m.p. 176°–179° C. (EtOH).

Analysis for C$_{11}$H$_{15}$NO$_4$S: Calculated %: C, 51.35; H, 5.88; N, 5.44. Found %: C, 51.20; H, 5.80; N, 5.51.

REFERENCE 15

2-Methoxy-5-(3-oxopentyl)benzenesulfonamide

Pale yellow needles, m.p. 135°–138° C. (EtOH).

Analysis for C$_{12}$H$_{17}$NO$_4$S Calculated % : C, 53.12; H, 6.32N, 5.16. Found % : C, 53.14; H, 6.27; N, 5.16.

REFERENCE 16

4-Methoxy-3-(2-oxopropyl)benzenesulfonamide

Pale yellow needles, m.p. 138°–139° C. (MeOH).

Analysis for C$_{10}$H$_{13}$NO$_4$S: Calculated % : C, 49.37; H, 5.39; N, 5.76. Found % : C, 49.23; H, 5.41; N, 5.60.

REFERENCE 17

2-Methoxy-5-(2-oxopropyl)-N-propylbenzenesulfonamide

Yellowish orange oil.

NMR spectrum δ(CDCl$_3$)ppm: 0.86 (3H,t,J=7.5 Hz), 1.47 (2H,sex,J=7 Hz), 2.19 (3H,s), 2.84 (2H,q,J=6.5 Hz), 3.72 (2H,s), 3.97 (3H,s), 5.03 (1H,t,J=6.5 Hz), 7.01 (1H,d,J=8.5 Hz), 7.38 (1H,d-d,J=8.5,2.5 Hz), 7.72 (1H,d,J=2 Hz).

High resolution mass spectrum for C$_{13}$H$_{19}$NO$_4$S: Calculated m/z: 285.1035. Found m/z: 285.1038.

REFERENCE 18

N,N-Diethyl-2-methoxy-5-(2-oxopropyl)benzenesulfonamide

Yellowish brown oil.

NMR spectrum δ(CDCl$_3$)ppm: 1.11 (6H,t,J=7 Hz), 2.17 (3H,s), 3.33 (4H,q,J=7 Hz), 3.68 (2H,s), 3.91 (3H,s), 6.95 (1H,d,J=8.5 Hz), 7.32 (1H,d-d,J=8.5,2 Hz), 7.75 (1H,d,J=2 Hz).

High resolution mass spectrum for C$_{14}$H$_{21}$NO$_4$S: Calculated m/z: 299.1191. Found m/z: 299.1179.

REFERENCE 19

N-Butyl-2-methoxy-5-(2-oxopropyl)benzenesulfonamide

Yellow oil.

NMR spectrum δ(CDCl$_3$)ppm: 0.68–0.98 (3H,m), 1.05–1.64 (4H,m), 2.19 (3H,s), 2.87 (2H,q,J=6.5 Hz), 3.72 (2H,s), 3.97 (3H,s), 4.96 (1H,t,J=6.5 Hz), 7.01 (1H,d,J=8.5 Hz), 7.38 (1H,d-d,J=8.5, 2.5 Hz), 7.72 (1H,d,J=2.5 Hz).

High resolution mass spectrum for C$_{14}$H$_{21}$NO$_4$S: Calculated m/z: 299.1191. Found m/z: 299.1180.

REFERENCE 20

N-Ethyl-2-methoxy-5-(2-oxopropyl)benzenesulfonamide

Yellow oil.

NMR spectrum δ(CDCl$_3$)ppm: 1.08 (3H,t,J=7 Hz), 2.19 (3H,s), 2.95 (2H,q,J=7 Hz), 3.72 (2H,s), 3.97 (3H,s), 7.02 (1H,d,J=8.5 Hz), 7.38 (1H,d-d,J=8.5, 2.5 Hz), 7.72 (1H,d,J=2.5 Hz).

High resolution mass spectrum for C$_{12}$H$_{17}$NO$_4$S: Calculated m/z: 271.0878. Found m/z: 271.0879.

REFERENCE 21

N-[[2-Methoxy-5-(2-oxopropyl)phenyl] sulfonyl] thiomorpholine

Yellow prisms, m.p. 118°–122° C. (EtOH).

Analysis for C$_{14}$H$_{19}$NO$_4$S$_2$: Calculated %: C, 51.04; H, 5.81; N, 4.25. Found %: C, 50.70; H, 6.07; N, 4.15.

REFERENCE 22

5-(2-Aminoethyl)-2-Methoxybenzenesulfonamide hydrochloride (1) To a solution of 14.9 g of trifluoro-N-[2-(4-methoxyphenyl)ethyl] acetamide in 45 ml of dichloromethane were added dropwise 21.1 g of chlorosulfonic acid with stirring under ice cooling. The reaction mixture was refluxed for 2 hours, poured into ice water and extracted with chloroform.

The extract was washed with water, dried and evaporated to give 13.5 g of a yellow oil. To 30 ml of ammonia water was added dropwise a solution of 13.5 g of the yellow oil in 20 ml of tetrahydrofuran with stirring under ice cooling and the reaction mixture was stirred for 30 minutes at room temperature. The solvent was removed and washed with water to give 10.6 g of 5-[2(trifluoroacetylamino)ethyl]-2-methoxybenzenesulfonamide as colorless crystals which were recrystallized from ethanol as colorless needles, m.p. 165°–166° C.

Analysis for C$_{11}$H$_{13}$F$_3$N$_2$O$_4$S: Calculated %: C, 40.49; H, 4.02; N, 8.59. Found %: C, 40.55; H, 4.26; N, 8.68.

(2) To a suspension of 10.0 g of 5-[2-(trifluoroacetylamino)ethyl]-2-methoxybenzenesulfonamide in 100 ml of methanol were added 60 ml of 10% sodium hydroxide aqueous solution with stirring at room temperature and the reaction mixture was stirred for 30 minutes. The reaction mixture was acidfied with 13 ml of hydrochloric acid. The precipitate was filtered and recrystallized from water to give 4.22 g of the desired compound as colorless needles, m.p. 263°–266° C.

Analysis for C$_9$H$_{14}$N$_2$O$_3$S.HCl: Calculated %: C, 40.52; H, 5.67; N, 10.50. Found %: C, 40.46; H, 5.50; N, 10.60.

In the same manner as described in Reference 22, the compounds of References 23 to 25 were prepared.

REFERENCE 23

5-(3-Aminopropyl)-2-methoxybenzenesulfonamide hydrochloride (1) 5-[3-(Trifluoroacetylamino)propyl]-2-methoxybenzenesulfonamide Colorless needles, m.p. 139°–143° C. (EtOH-Et$_2$O).

Mass spectrum: m/z: 340 (M+).

NMR spectrum δ(DMSO-d$_6$)ppm: 1.77 (2H,t-t,J=7.5,7 Hz), 2.61 (2H,t,J=7.5 Hz), 3.21 (2H,t,J=7 Hz), 3.88 (3H,s), 6.84 (2H,br s), 7.10 (1H,d,J=8.5 Hz), 7.39 (1H,d-d,J=8.5,2 Hz), 7.59 (1H,d,J=2 Hz), 9.28 (1H,br s).

(2) 5-(3-Aminopropyl)-2-methoxybenzenesulfonamide hydrochloride

Colorless scales, m.p. 255°–257° C. (EtOH-H$_2$O).

Analysis for C$_{10}$H$_{16}$N$_2$O$_3$S.HCl: Calculated %: C, 42.78; H, 6.10; N, 9.98. Found %: C, 42.83; H, 6.15; N, 9.97.

REFERENCE 24

5-(4-Aminobutyl)-2-methoxybenzenesulfonamide hydrochloride (1) 2-Methoxy-5-[4-(trifluoroacetylamino)butyl]benzenesulfonamide [Starting material, trifluoro-N-[4-(4-methoxyphenyl)butyl]-acetamide (m.p. 67°–68° C.(iso-Pr$_2$O), colorless plates), was obtained by treatment of 4-(4-methoxyphenyl)butylamide with anhydrous trifluoroacetic acid.]

Colorless needles, m.p. 145°–147° C.(EtOH).

Analysis for C$_{13}$H$_{17}$F$_3$N$_2$O$_4$S: Calculated %: C, 44.06; H, 4.84; N, 7.91. Found %: C, 43.77; H, 4.99; N, 7.88.

(2) 5-(4-Aminobutyl)-2-methoxybenzenesulfonamide hydrochloride

Colorless needles, m.p. 178°–181° C. (H$_2$O)

NMR spectrum δ (CD$_3$OD)ppm: 1.48–1.92(4H, m), 2.51–3.19 (4H,m), 3.96(3H,s), 7.12(1H,d,J=8.5Hz), 7.44(1,d-d,J=8.5,2Hz), 7.68(1H,d,J=2Hz).

High resolution mass spectrum for C$_{11}$H$_{18}$N$_2$O$_3$S: Calculated m/z: 258.1038. Found m/z: 258.1035.

REFERENCE 25

5-(2-Aminobutyl)-2-methoxybenzenesulfonamide hydrochloride (1) 2-Methoxy-5-[2(trifluoroacetylamino)butyl]benzenesulfonamide [Starting material, trifluoro-N-[1-(4-methoxyphenylmethyl)-propyl]acetamide (m.p. 82°–83° C. (iso-Pr$_2$O), colorless needles), was obtained by treatment of 1-(4-methoxyphenyl methyl)propylamine with anhydrous trifluoroacetic acid]

Colorless needles, m.p. 189°–192° C. (EtOH).

Analysis for C$_{13}$H$_{17}$F$_3$N$_2$O$_4$S: Calculated %: C, 44.06; H, 4.84; N, 7.91. Found %: C, 43.85; H, 5.09; N, 7.91.

(2) 5-(2-Aminobutyl)-2-methoxybenzenesulfonamide hydrochloride

Colorless prisms, m.p. 246°–250° C. (MeOH).

Analysis for C$_{11}$H$_{18}$N$_2$O$_3$S.HCl: Calculated %: C, 44.82; H, 6.50; N, 9.50. Found %: C, 44.56; H, 6.29; N, 9.42.

REFERENCE 26

2-(5-Fluoro-2-methoxyphenoxy)ethylamine (1) A suspension of 8.75 g of 5-fluoro-2-methoxyphenol, 10.9 g of ethylene carbonate and 8.50 g of potassium carbonate in 12 ml of toluene was refluxed for 2.5 hours. The reaction mixture was diluted with benzene, washed with water, dried and evaporated. The residue was distilled to give 9.15 g of 2-(5-fluoro-2-methoxyphenoxy)ethanol as colorless oil, b.p. 138°–140° C. (8mmHg).

Mass spectrum: m/z: 186 (M+).

NMR spectrum δ(CDCl$_3$) ppm: 2.96 (1H,s), 3.58–4.30 (4H,m), 3.83 (3H,s), 6.48–6.92 (3H,m).

(2) To a solution of 9.00 g of 2-(5-methoxyphenoxy) ethanol in 4.5 ml of pyridine were added dropwise 3.9 ml of thionylchloride with stirring under ice cooling. The reaction mixture was heated for 2 hours at 80°–90° C., poured into 40 ml of 10% hydrochloric acid and extracted with chloroform. The extract was washed with water, dried and evaporated. The residue was distilled to give 8.50 g of 2-(2-chloroethoxy)-4-fluoroanisole as a colorless oil, b.p. 118°–120° C. (6 mmHg), which were solidified as crystals of m.p. 35°–38° C.

Mass spectrum m/z: 204,206 (3:1 M+).

NMR spectrum δ(CDCl$_3$) ppm: 3.82 (2H,t,J=6.5Hz), 3.83 (3H,s), 4.24 (2H,t,J=6.5Hz), 6.48–6.96 (3H,m).

(3) A suspension of 8.00 g of 2-(2-chloroethoxy)-4-fluoroanisole, 5.75 g of phthalimide and 3.24 g of potassium carbonate in 15 ml of N,N-dimethylformamide was heated for 2 hours at 120°–130° C. After cooling, the reaction mixture was poured into water. The precipitate was filtered to give 10.4 g of N-[2-(5-fluoro-2-methoxyphenoxy)ethyl]phthalimide as colorless crystals, which were recrystallized from ethanol as colorless needles, m.p. 134.5°–136° C.

Analysis for C$_{17}$H$_{14}$FNO$_4$: Calculated %: C, 64.76; H, 4.48; N, 4.44. Found %: C, 64.88; H, 4.72; N, 4.39.

(4) A suspension of 10.0 g of N-[2-(5-fluoro-2-methoxyphenoxy)ethyl]phthalimide and 5.14 ml 5.14 ml of hydrazine hydrate in 100 ml of ethanol was heated for 1 hour at 50°–60° C. After cooling, the precipitate was filtered off and the filtrate was evaporated. The residue was diluted with water and extracted with chloroform. The extract was washed with water, dried and evaporated. The residue was distilled to give 3.81 g of the desired compound as a colorless oil, b.p. 126°–127° C. (9 mmHg).

NMR spectrum δ(CDCl$_3$)ppm: 1.45 (2H,s), 3.09 (2H,t,J=5.5Hz), 3.82 (3H,s), 3.99 (2H,t,J=5.5Hz), 6.44–6.90 (3H,m).

High resolution mass spectrum for C$_9$H$_{12}$FNO$_2$: Calculated m/z: 185.0852. Found m/z: 185.0852.

In the same manner as described in Reference 26, the compounds of References 27 to 32 were prepared.

REFERENCE 27

2-(4-Fluoro-2-methoxyphenoxy)ethylamine (1) 2-(4-Fluoro-2-methoxyphenoxy)ethanol Colorless oil, b.p. 147°–150° C. (9 mmHg).

Mass spectrum: m/z: 186(M+).

NMR spectrum δ(CDCl$_3$) ppm: 2.95 (1H,s), 3.83 (3H,s), 3.90 (2H,t,J=4Hz), 4.07(2H,t,J=4Hz), 6.45–6.94(3H,m).

(2) 2-Chloroethoxy-5-fluoroanisole

Colorless crystals, m.p. 30°–34° C., b.p 120–125° C. (8 mmHg).

Mass spectrum m/z: 204,206(3:1,M+).

NMR spectrum δ(CDCl$_3$) ppm: 3.79(2H,t,J=6Hz), 3.85 (3H,s), 4.23(2H,t,J=6Hz), 6.45–6.95(3H,m).

(3) N-[2-(4-Fluoro-2-methoxyphenoxy)ethyl]phthalimide

Colorless needles, m.p. 102°–104° C. (EtOH).

Analysis for C$_{17}$H$_{14}$FNO$_4$: Calculated %: C, 64.76; H, 4.48; N, 4.44. Found %: C, 64.86; H, 4.60; N, 4.31.

(4) 2-(4-Fluoro-2-methoxyphenoxy)ethylamine

Colorless oil, b.p. 127°–130° C. (10 mmHg).

NMR spectrum δ(CDCl$_3$) ppm: 1.55(2H,s), 3.07 (2H,t,J=5Hz), 3.84 (3H,s), 4.00 (2H,t,J=5Hz), 6.48–6.91(3H,m).

High resolution mass spectrum for C$_9$H$_{12}$FNO$_2$: Calculated m/z : 185.0852. Found m/z : 185.0850.

REFERENCE 28

2-(3-Fluoro-2-methoxyphenoxy)ethylamine (1) 2-(3-Fluoro-2-methoxyphenoxy)ethanol Colorless oil.

Mass spectrum m/z: 186(M+).

NMR spectrum δ(CDCl$_3$) ppm: 2.40 (1H,s), 3.93 (3H,d,J=1Hz), 3.80–4.20 (4H, m), 6.60–7.08 (3H,m).

(2) 2-(2-Chloroethoxy)-6-fluoroanisole
Colorless oil.

Mass spectrum m/z: 204,206(3:1,M+).

NMR spectrum δ(CDCl$_3$) ppm: 3.84 (2H, t,J=6 Hz), 3.94 (3H,d,J=0.5 Hz), 4.28 (2H,t,J=6 Hz), 6.59–7.10(3H, m).

(3) N-[2-(3-Fluoro-2-methoxyphenoxy)ethyl]phthalimide

Colorless scales, m.p. 112°–113° C. (EtOH).

Analysis for C$_{17}$H$_{14}$FNO$_4$: Calculated %: C, 64.76; H, 4.48; N, 4.44. Found %: C, 64.57; H, 4.48; N, 4.42.

(4) 2-(3-Fluoro-2-methoxyphenoxy)ethylamine
Pale yellow oil.

NMR spectrum δ(CDCl$_3$) ppm: 1.63 (2H,s), 3.11 (2H,t,J=5 Hz), 3.92 (3H,d,J=1 Hz), 4.04 (2H,t,J=5 Hz), 6.56–7.08(3H,m).

High resolution mass spectrum for C$_9$H$_{12}$FNO$_2$: Calculated m/z: 185.0852. Found m/z: 185.0860.

REFERENCE 29

2-(2-Ethoxy-5-fluorophenoxy)ethylamine (1) 2-(2-Ethoxy-5-fluorophenoxy)ethanol
Colorless oil, b.p. 141°–145° C. (11mmHg).

Mass spectrum: m/z: 200(M+).

NMR spectrum δ(CDCl$_3$) ppm: 1.41 (3H,t,J=7 Hz), 3.00 (1H,s), 3.85–4.16 (6H,m), 6.52–6.89 (3H,m).

(2) 2-(2-Chloroethoxy)-1-ethoxy-4-fluorobenzene
Pale yellow oil, b.p. 120°–122° C. (7mmHg).

Mass spectrum m/z: 218,220(3:1,M+).

NMR spectrum δ(CDCl$_3$) ppm: 1.41 (3H,t,J=7 Hz), 3.82 (2H,t,J=6 Hz), 4.04 (2H,q,J=7 Hz), 4.24 (2H,t,J=6 Hz), 6.54–6.93 (3H,m).

(3) N-[2-(2-Ethoxy-5-fluorophenoxy)ethyl]phthalimide

Colorless needles, m.p. 119°–121° C. (EtOH).

Analysis for C$_{18}$H$_{16}$FNO$_4$: Calculated %: C, 65.65; H, 4.90; N, 4.25. Found %: C, 65.69; H, 4.96; N, 4.25.

(4) 2-(2-Ethoxy-5-fluorophenoxy)ethylamine
Colorless oil, b.p. 129°–131° C. (8mmHg).

NMR spectrum δ(CDCl$_3$) ppm: 1.41 (3H,t,J=7 Hz), 1.66 (2H,s), 3.09 (2H,t,J=5 Hz), 4.00 (2H,t,J=5 Hz), 4.04 (2H,q,J=7 Hz), 6.50–6.80 (3H,m).

High resolution mass spectrum for C$_{10}$H$_{14}$FNO$_2$: Calculated m/z: 199.1009. Found m/z: 199.1010.

REFERENCE 30

2-(2-Butoxy-5-fluorophenoxy)ethylamine (1) 2-(2-Butoxy-5-fluorophenoxy)ethanol
Colorless oil, b.p. 128°–130° C. (5mmHg).

Mass spectrum: m/z: 228(M+).

NMR spectrum δ(CDCl$_3$) ppm: 0.97 (3H,t,J=6.5 Hz), 1.17–2.07 (4H,m), 2.88 (1H,s), 3.74–4.28 (6H,m), 6.40–7.03 (3H,m).

(2) 1-Butoxy-2-(2-chloroethoxy)-4-fluorobenzene
Colorless oil, b.p. 104°–106° C. (6mmHg).

Mass spectrum m/z: 246,248 (3:1,M+).

NMR spectrum δ(CDCl$_3$) ppm: 0.97 (3H,t,J=6.5 Hz), 1.22–2.15 (4H,m), 3.81 (2H,t,J=6Hz), 3.97 (2H,t,J=6.5 Hz), 4.24 (2H,t,J=6 Hz), 6.40–7.04 (3H,m).

(3) N-[2-(2-Butoxy-5-fluorophenoxy)ethyl]phthalimide

Colorless needles, m.p. 107°–108° C. (MeOH).

Analysis for C$_{20}$H$_{20}$FNO$_4$: Calculated %: C, 67.22; H, 5.64; N, 3.92. Found %: C, 67.08; H, 6.02; N, 3.73.

(4) 2-(2-Butoxy-5-fluorophenoxy)ethylamine
Pale yellow oil, b.p. 120°–122° C. (6mmHg).

NMR spectrum δ(CDCl$_3$) ppm: 0.98 (3H,t,J=6.5 Hz), 1.19–2.11 (4H,m), 1.58 (2H,s), 3.09 (2H,t,J=5 Hz), 3.96 (2H,t,J=6.5 Hz), 3.99 (2H,t,J=5 Hz), 6.40–6.96 (3H,m).

High resolution mass spectrum for C$_{12}$H$_{18}$FNO$_2$: Calculated m/z: 227.1322. Found m/z: 227.1325.

REFERENCE 31

2-(5-Fluoro-2-propoxyphenoxy)ethylamine (1) 2-(5-Fluoro-2-propoxyphenoxy)ethanol
Colorless oil, b.p. 136°–140° C. (8mmHg).

Mass spectrum m/z: 214(M+).

NMR spectrum δ(CDCl$_3$) ppm: 1.03 (3H,t,J=7 Hz), 1.82 (2H,sex,J=7 Hz), 2.54 (1H,s), 3.49–4.42 (6H,m), 6.38–7.00 (3H,m).

(2) 2-(2-chloroethoxy)-4-fluoro-1-propoxybenzene
Colorless oil, b.p. 117°–121° C. (8mmHg).

Mass spectrum m/z: 232,234 (3:1,M+).

NMR spectrum δ(CDCl$_3$) ppm: 1.04 (3H,t,J=7 Hz), 1.81 (2H,sex,J=7 Hz), 3.81 (2H,t,J=6.5 Hz), 3.93 (2H,t,J=7 Hz), 4.24 (2H,t,J=6.5 Hz), 6.40–7.04 (3H,m).

(3) N-[2-(5-Fluoro-2-propoxyphenoxy)ethyl]phthalimide

Colorless needles, m.p. 102°–103° C. (MeOH).

Analysis for C$_{19}$H$_{18}$FNO$_4$: Calculated %: C, 66.46; H, 5.28; N, 4.08. Found %: C, 66.50; H, 5.24; N, 4.07.

(4) 2-(5-Fluoro-2-propoxyphenoxy)ethylamine
Pale yellow oil, b.p. 138°–140° C. (9 mmHg).

NMR spectrum δ (CDCl$_3$) ppm: 1.03 (3H,t,J=7 Hz), 1.68 (2H,s), 1.82 (2H,sex,J=7 Hz), 3.09 (2H,t,J=5 Hz), 3.91 (2H,t,J=7 Hz), 3.99 (2H,t,J=5 Hz), 6.40–6.96 (3H,m).

High resolution mass spectrum for C$_{11}$H$_{16}$FNO$_2$: Calculated m/z: 213.1165. Found m/z: 213.1165.

REFERENCE 32

2-(5-Fluoro-2-methoxyphenoxy)acetaldehyde (1) 2-(5-Fluoro-2-methoxyphenoxy)acetaldehyde diethylacetal A suspension of 10.8 g of 5-fluoro-2-methoxyphenol and 12.6 g of potassium carbonate in 45 ml of N,N-dimethylformamide was heated for 45 minutes at 100° C. To the reaction mixture were added 18.5 ml of chloroacetaldehyde diethylacetal and 12.7 g of potassium iodide and the reaction mixture was heated for 4 hours at 140° C. After cooling, the reaction mixture was poured into ice water and extracted with ether. The extract was washed with aqueous sodium hydroxide solution and water, dried and evaporated. The residue was chromatographed on silica gel using chloroform as an eluant to give 11.8 g of the desired compound as a colorless oil.

Mass spectrum: m/z: 258 (M+).

NMR spectrum δ (CDCl$_3$) ppm: 1.24 (6H,t,J=7 Hz), 3.53-3.88 (4H,m), 3.82 (3H,s), 4.03 (2H,d,J=5 Hz), 4.87 (1H,t,J=5 Hz), 6.48-6.88 (3H,m).

(2) 2-(5-Fluoro-2-methoxyphenoxy)acetaldehyde

To a solution of 23.0 g of 2-(5-fluoro-2-methoxyphenoxy)acetaldehyde diethylacetal in 130 ml of acetone were added 100 ml of 10% aqueous oxalic acid and the mixture was refluxed for 2 hours. After cooling, the reaction mixture was evaporated, and the residue was diluted with water and extracted with ether. The extract was washed with water, dried and evaporated. Isopropyl ether was added to the residue and the precipitate was filtered to give 4.99 g of the desired compound as pale brown crystals, which were recrystallized from a mixture of isopropanol and isopropyl ether as pale brown crystals, m.p. 92.5°-95° C.

High resolution mass spectrum for C$_9$H$_9$FO$_3$: Calculated m/z: 184.0536. Found m/z: 184.0532.

EXAMPLE 1

5-[2-[2-(5-Fluoro-2-methoxyphenoxy)ehtylamino]-propyl]-2-methoxybenzenesulfonamide hydrochloride A solution of 0.92 g of 2-methoxy-5-(2-oxopropyl)-benzenesulfonamide and 0.70 g of 2-(5-fluoro-2-methoxyphenoxy)ethylamine in 30 ml of methanol was refluxed for 2 hours. To the solution were added 0.23 g of sodium borohydride under ice cooling and the solution was stirred for 1 hour at room temperature. The reaction mixture was evaporated and acidified with 30 ml of 10% hydrochloric acid. The precipitate was filtered and recrystallized from a mixture of methanol and ether to give 0.69 g of the desired compound as pale yellow needles, m.p.258-261° C.

NMR spectrum δ (DMSO-d$_6$) ppm: 1.17 (3H,d,J=6.5 Hz), 2.60-3.70 (5H,m), 3.76 (3H,s), 3.90 (3H,s), 4.37 (2H,t,J=5.5 Hz), 6.60-7.25 (4H,m), 7.46 (1H,d-d,J=8.5,2.5 Hz), 7.64 (1H,d,J=2.5 Hz), 9.37 (2H,br s).

Analysis for C$_{19}$H$_{25}$FN$_2$O$_5$S.HCl: Calculated %: C, 50.83; H, 5.84; N, 6.24. Found %: C, 50.83; H, 5.82; N, 6.14.

In the usual manner, the following acid addition salts were prepared.

| | |
|---|---|
| Phosphate Colorless needles, | m.p.194-195° C. (MeOH). |
| Nitrate Colorless needles, | m.p.181-184° C. (EtOH). |
| Hydrobromide Colorless crystals, | m.p.252-254° C. (MeOH). |
| Maleate Colorless crystals, | m.p.100-105° C. (EtOH). |
| Mandelate Colorless prisms, | m.p.168-170° C. (MeOH). |
| Succinate Colorless prisms, | m.p.160-165° C. (EtOH). |
| ½ Succinate Colorless plates, | m.p.164-166° C. (MeOH). |
| Fumarate Colorless prisms, | m.p.207-212° C. (MeOH—H$_2$O). |
| ½ Fumarate Colorless needles, | m.p.215-216.5° C. (MeOH). |
| p-Toluenesulfonate Colorless prisms, | m.p.168-171° C. (EtOH). |
| DL-10-Camphorsulfonate Colorless crystals, | m.p.196-197° C. (MeOH). |

In the same manner as described in Example 1, the compounds of Examples 2 to 29 were prepared.

EXAMPLE 2

2-Ethoxy-5-[2-[2-(5-fluoro-2-methoxyphenoxy)ethylamino]propyl] benzenesulfonamide hydrochloride Pale brown crystals, m.p. 240°-243° C. (MeOH).

Analysis for C$_{20}$H$_{27}$FN$_2$O$_5$S'HCl: Calculated %: C, 51.89; H, 6.10; N, 6.05. Found %: C, 51.60; H, 6.01; N, 5.98.

EXAMPLE 3

2-Ethoxy-5-[2-[2-(5-fluoro-2-methoxyphenoxy)ethylamino]-N-methylbenzenesulfonamide oxalate Pale yellow crystals, m.p. 215°-218° C. (EtOH-H$_2$O).

Analysis for C$_{21}$H$_{29}$FN$_2$O$_5$S.C$_2$H$_2$O$_4$: Calculated %: C, 52.07; H, 5.89; N, 5.28. Found %: C, 52.24; H, 6.16; N, 5.09.

EXAMPLE 4

2-Ethoxy-5-[2-[2-(5-fluoro-2-methoxyphenoxy)ethylamino]-N,N-dimethylbenzenesulfonamide oxalate Colorless crystals, m.p. 225°-227° C. (EtOH-H$_2$O).

Analysis for C$_{22}$H$_{31}$FN$_2$O$_2$S.C$_2$H$_2$O$_4$: Calculated %: C, 52.93; H, 6.11; N, 5.14. Found %: C, 52.58; H, 6.04; N, 5.11.

EXAMPLE 5

2-Ethoxy-5-[2-[2-(2-ethoxy-5-fluorophenoxy)ethylamino]propyl] benzenesulfonamide hydrochloride Pale brown crystals, m.p. 196°-198° C. (EtOH).

Analysis for C$_{21}$H$_{29}$FN$_2$O$_5$S'HCl: Calculated %: C, 52.88; H, 6.34; N, 5.87. Found %: C, 52.55; H, 6.22; N, 5.76.

EXAMPLE 6

2-Ethoxy-5-[2-[2-(4-fluoro-2-methoxyphenoxy)ethylamino]propyl] benzenesulfonamide hydrochloride Pale brown crystals, m.p. 261°-264° C. (EtOH-H$_2$O).

Analysis for C$_{20}$H$_{27}$FN$_2$O$_5$S'HCl: Calculated %: C, 51.89; H, 6.10; N, 6.05. Found %: C, 51.63; H, 6.00; N, 5.88.

EXAMPLE 7

5-[3-[2-(5-Fluoro-2-methoxy phenoxy)ethylamino]pentyl]-2-methoxybenzenesulfonamide hydrochloride Colorless crystals, m.p. 198°-201° C. (MeOH-Et$_2$O).

Analysis for C$_{21}$H$_{29}$FN$_2$O$_5$S'HCl: Calculated %: C, 52.88; H, 6.34; N, 5.87. Found %: C, 52.67; H, 6.24; N, 5.87.

EXAMPLE 8

5-[3-[2-(5-Fluoro-2-methoxyphenoxy)ethylamino]-butyl]-2-methoxybenzenesulfonamide Colorless oil.

NMR spectrum δ (CDCl$_3$) ppm: 1.14 (3H,d,J=6 Hz), 1.46-1.90 (2H,m), 2.49-3.13 (5H,m), 3.81 (3H,s), 3.97 (3H,s), 4.08 (2H,t,J=5.5 Hz), 6.48-6.85 (3H,m), 6.93 (1H,d,J=8.5 Hz), 7.36 (1H,d-d,J=8.5,2.5 Hz), 7.74 (1H,d,J=2.5 Hz)

High resolution mass spectrum for C$_{20}$H$_{27}$FN$_2$O$_5$S: Calculated m/z: 426.1625. Found m/z: 426.1643.

EXAMPLE 9

5-[2-[2-(5-Fluoro-2-methoxyphenoxy)ethylamino]-propyl]-2-methoxy-N-methylbenzenesulfonamide oxalate Colorless crystals, m.p. 234°-235° C. (EtOH-H$_2$O).
Analysis for $C_{20}H_{27}FN_2O_5S'C_2H_2O_4$: Calculated %: C, 51.16; H, 5.66; N, 5.42. Found % : C, 51.03; H, 5.67; N, 5.39.

EXAMPLE 10

5-[2-[2-(5-Fluoro-2-methoxyphenoxy)ethylamino]-propy]-2-methoxy-N,N-dimethylbenzenesulfonamide oxalate Colorless crystals, m.p. 225°-227° C. (EtOH-H$_2$O).
Analysis for $C_{21}H_{29}FN_2O_5S.C_2H_2O_4$: Calculated %: C, 52.07; H, 5.89; N, 5.28. Found %: C, 51.93; H, 5.92; N, 5.30

EXAMPLE 11

1-[[5-[2-[2-(5-Fluoro-2-methoxyphenoxy)ethylamino]-propyl]-2methoxyphenyl]sulfonyl]pyrrolidine oxalate Colorless crystals, m.p. 205°-207° C. (MeOH).
Analysis for $C_{23}H_{31}FN_2O_5S. C_2H_2O_4$: Calculated %: C, 53.95; H, 5.98; N, 5.03. Found %: C, 53.83; H, 5.96; N, 5.01.

EXAMPLE 12

1-[[5-[2-[2-(5-Fluoro-2-methoxyphenoxy)ethylamino]-propyl]-2-methoxyphenyl]sulfonyl]-methoxyphenyl]-sulfonyl]piperidine oxalate Cololess crystals, m.p. 182°-184° C. (MeOH).
Analysis for $C_{24}H_{33}FN_2O_5S.C_2H_2O_4$: Calculated %: C, 54.73; H, 6.18; N, 4.91. Found %: C, 54.56; H, 6.05; N, 4.89.

EXAMPLE 13

1-[[5-[2-[(2-(5-Fluoro-2-methoxyphenoxy)ethylamino]-propyl]-2-methoxyphenyl]sulfonyl]4-methylpiperazine Pale yellow oil.
NMR spectrum δ(CDCl$_3$) ppm: 1.04 (3 H,d,J=6 Hz), 1.91 (1H,s), 2.28 (3H,s), 2.35-3.50 (13H,m), 3.80 (3H,s), 3.88 (3H,s), 4.06 (2H,t,J=5.5 Hz), 6.45-6.85(3H,m), 6.92(1H,d,J=8.5 Hz), 7.34(1H,d-d, J=8.5, 2 Hz), 7.70 (1H,d,J=2 Hz)
High resolution mass spectrum for $C_{24}H_{34}FN_3O_5S$: Calculated m/z: 495.2203. Found m/z: 495.2210.

EXAMPLE 14

5-[2-[2-(2-Ethoxy-5-fluorophenoxy)ethylamino]-propyl]-2-methoxybenzenesulfonamide hydrochloride Colorless needles, m.p. 236°-241° C. (EtOH-H$_2$O).
Analysis for $C_{20}H_{27}FN_2O_5S.HCl$:
Calculated %: C, 51.89; H, 6.10; N, 6.05.
Found %: C, 51.85; H, 6.02; N, 5.97.

EXAMPLE 15

5-[2-[2-(2-Ethoxy-5-fluorophenoxy)ethylamino]-propyl]-2-methoxy-N,N-dimethylbenzenesulfonamide oxalate Colorless crystals, m.p. 173°-175° C. (MeOH).
Analysis for $C_{22}H_{31}FN_2O_5S.C_2H_2O_4$: Calculated %: C, 52.93; H, 6.11; N, 5.14. Found %: C, 52.91; H, 6.10; N, 5.21.

EXAMPLE 16

5-[2-[2(3-Fluoro-2-methoxyphenoxy)ethylamino]-propyl]-2-methoxybenzenesulfonamide hydrochloride Colorless scales, m.p. 211°-212°C. (MeOH).
Analysis for $C_{19}H_{25}FN_2O_5S.HCl.\frac{1}{2}H_2O$: Calculated %: C, 49.83; H, 5.94; N, 6.12. Found %: C, 50.03; H, 5.81; N, 6.12.

EXAMPLE 17

5-[2-[2-(4-Fluoro-2-methoxyphenoxy)ethylamino]-propyl]-2-methoxybenzenesulfonamide hydrochloride Colorless crystals, m.p. 257°-259° C. (EtOH-H$_2$O).
Analysis for $C_{19}H_{25}FN_2O_5S.HCl$: Calculated %: C, 50.83; H, 50.83; N, 6.24. Found %: C, 50.78; H, 5.65; N, 6.22.

EXAMPLE 18

3-[2-[2-(5-Fluoro-2-methoxyphenoxy)ethylamino]propyl]-4-methoxybenzenesulfonamide oxalate Colorless crystals, m.p. 111°-114° C. (MeOH).
Analysis for $C_{19}H_{25}FN_2O_5S.C_2H_2O_4.H_2O$: Calculated %: C, 48.46; H, 5.62; N, 5.38. Found %: C, 48.16; H, 5.63; N, 5.25.

EXAMPLE 19

N,N-Diethyl-5-[2-[2-(5-fluoro-2-methoxyphenoxy)ethylamino]propyl]-2-methoxybenzenesulfonamide oxalate Colorless prisms, m.p. 165.5°-168° C. (MeOH).
Analysis for $C_{23}H_{33}FN_2O_5S.C_2H_2O_4$: Calculated %: C, 53.75; H, 6.32; N, 5.01. Found %: C, 53.55; H, 6.04; N, 4.94.

EXAMPLE 20

5-[2[2-(5-Fluoro-2-methoxyphenoxy)ethylamino]-propyl]-2-methoxy-N-propylbenzenesulfonamide ½fumarate Colorless crystals, m.p. 168°-170° C. (MeOH-Et$_2$O).
Analysis for $C_{22}H_{31}FN_2O_5S. \frac{1}{2}C_4H_4O_4$: Calculated %: C, 56.24; H, 6.49; N, 5.46. Found %: C, 55.98; H, 6.27; N, 5.40.

EXAMPLE 21

N-Ethyl-5-[2-(5-fluoro-2-methoxyphenoxy)ethylamino]propyl]-2-methoxy-benzenesulfonamide oxalate Colorless crystals, m.p. 207°-209° C. (EtoH-H$_2$O).
Analysis for $C_{21}H_{29}FN_2O_5S.C_2H_2O_4$: Calculated %: C, 52.07; H, 5.89; N, 5.28. Found %: C, 51.77; H, 5.92; N, 5.08.

EXAMPLE 22

N-Butyl-5-[2-[2-(5-fluoro-2-methoxyphenoxy)ethylamino]propyl]-2-methoxybenzenesulfonamide oxalate Colorless crystals, m.p. 173°-175 ° C. (MeOH).
Analysis for $C_{23}H_{33}FN_2O_5S.C_2H_2O_4$: Calculated %: C, 53.75; H, 6.32; N,5.01. Found %: C, 53.66; H, 6.27; N, 4.99.

EXAMPLE 23

5-[2-2(5-Fluoro-2-propoxyphenoxy)ethylamino]-propyl]-2-methoxybenzenesulfonamide hydrochloride Colorless needles, m.p. 199°–202° C. (MeOH).
Analysis for $C_{21}H_{29}FN_2O_5S\cdot HCl$: Calculated %: C, 52.88; H, 6.34; N, 5.87. Found %: C, 52.91; H, 6.37; N, 5.65.

EXAMPLE 24

5-[2-[2-(2-Butoxy-5-fluorophenoxy)-ethylamino]-propyl]-2-methoxybenzenesulfonamide hydrochloride Colorless needles, m.p. 207°–209° C. (meOH).
Analysis for $C_{22}H_{31}FN_2O_5S\cdot HCl$: Calculated %: C, 53.81; H, 6.57; N, 5.71. Found %: C, 53.57; H, 6.57; N, 5.54.

EXAMPLE 25

5-[2-[2-(5-Fluoro-2-methoxyphenoxy)-ethylamino]-propyl]-2-propoxybenzenesulfonamide hydrochloride Colorless needles, m.p. 228°–232° C. (MeOH-H₂O).
Analysis for $C_{21}H_{29}FN_2O_5S\cdot HCl$: Calculated %: C, 52.88; H, 6.34; N, 5.87. Found %: C, 52.81; H, 6.35; N, 5.85.

EXAMPLE 26

5-[4-[2-(5-Fluoro-2-methoxyphenoxy)-ethylamino]pentyl]-2-methoxybenzenesulfonamide hydrochloride Pale brown crystals, m.p. 181°–183° C. (EtOH).
Analysis for $C_{21}H_{29}FN_2O_5S\cdot HCl$: Calculated %: C, 52.88; H, 6.34; N, 5.87. Found %: C, 52.64; H, 6.39; N, 5.83.

EXAMPLE 27

2-Butoxy-5-[2-[2-(5-Fluoro-2-methoxyphenoxy)-ethylamino]propyl] benzenesulfonamide hydrochloride Colorless needles, m.p. 227°–231° C. (MeOH-H₂O).
Analysis for $C_{22}H_{31}FN_2O_5S\cdot HCl$: Calculated %: C, 53.81; H, 6.57; N, 5.71. Found %: C, 53.56; H, 6.73; N, 5.65.

EXAMPLE 28

N-[[5-[2-[2-(5-Fluoro-2-methoxyphenoxy)-ethylamino]-propyl]-2-methoxyphenyl] sulfonyl]-morpholine oxalate Colorless crystals, m.p. 173°–174.5° C. (MeOH).
Analysis for $C_{33}H_{31}FN_2O_6S\cdot C_2H_2O_4$: Calculated %: C, 52.44; H, 5.81; N, 4.89. Found %: C, 52.35; H, 5.81; N, 4.68.

EXAMPLE 29

N-[[5-[2-[2-(5-Fluoro-2-methoxyphenoxy)-ethylamino]-propyl]-2-methoxyphenyl] sulfonyl]-thiomorpholine oxalate Pale yellow crystals, m.p. 181°–183° C. (MeOH).
Analysis for $C_{23}H_{31}FN_2O_5S_2\cdot C_2H_2O_4$: Calculated %: C, 51.01; H, 5.65; N, 4.76. Found %: C, 50.71; H, 5.59; N, 4.66.

EXAMPLE 30

5-[2-[2-(5-Fluoro-2-methoxyphenoxy)-ethylamino]ethyl]-2-methoxybenzenesulfonamide A suspension of 1.50 g of 5-(2-aminoethyl)-2-methoxybenzenesulfonamide hydrochloride and 0.8 ml of triethylamine in 50 ml of methanol was heated for 30 minutes at 75° C. To the reaction mixture was added 1.00 g of 2-(5-fluoro-2-methoxyphenoxy)acetaldehyde and the reaction mixture was heated for 10 minutes at 75° C. To the solution was added 0.45 g of sodium borohydride under ice cooling and the solution was stirred for 1 hr at room temperature. The reaction mixture was evaporated, acidified with 10% hydrochloric acid and washed with ether. The aqueous layer was made alkaline with potassium carbonate and extracted with ethyl acetate. The extract was washed with water, dried and evaporated. The residue was solidified with a mixture of methanol and ether and the precipitate was filtered to give 0.46 g of the desired compound as pale brown crystals which were recrystallized from N,N-dimethylformamide as pale yellow crystals, m.p. 201°–205° C.

Analysis for $C_{18}H_{23}FN_2O_5S$: Calculated %: C, 54.26; H, 5.82; N, 7.03. Found %: C, 53.87; H, 5.89; N, 6.83.

In the same manner as described in Example 30, the compounds of Examples 31 to 33 were prepared.

EXAMPLE 31

5-[3-[2-(5-Fluoro-2-methoxyphenoxy)-ethylamino]-propyl]-2-methoxybenzenesulfonamide Yellowish brown oil.
NMR spectrum δ (DMSO-d₆) ppm: 1.46–1.92 (2H,m), 2.42–3.04 (6H,m), 3.76 (3H,s), 3.91 (3H,s), 6.47–6.96 (3H,m), 7.05 (1H,d,J=8.5 Hz), 7.33 (1H,d—d,J=8.5,2 Hz), 7.55 (1H,d,J=2 Hz).
High resolution mass spectrum for $C_{19}H_{25}FN_2O_5S$: Calculated m/z: 412.1468. Found m/z: 412.1474.

EXAMPLE 32

5-[4-[2-(5-Fluoro-2-methoxyphenoxy)-ethylamino]-butyl]-2-methoxybenzenesulfonamide Yellowish brown oil.
NMR spectrum δ (DMSO-d₆) ppm: 1.04–1.76 (4H,m), 2.32–2.98 (6H,m), 3.69 (3H,d,J=2.5 Hz), 3.86 (3H,s), 3.96–4.18 (2H,m), 6.48–7.17 (3H,m), 7.06 (1H,d,J=8.5 Hz), 7.33 (1H,d—d,J=8.5,1.5 Hz), 7.53 (1H,d,J=1.5 Hz).
High resolution mass spectrum for $C_{20}H_{27}FN_2O_3S$: Calculated m/z: 426.1625. Found m/z: 426.1623.

EXAMPLE 33

5-[2-[2-(5-Fluoro-2-methoxyphenoxy)-ethylamino]-butyl]-2-methoxybenzenesulfonamide hydrochloride Colorless scales, m.p. 216°–219° C. (MeOH).
Analysis for $C_{26}H_{27}FN_2O_5S\cdot HCl$: Calculated %: C, 51.89; H, 6.10; N, 6.05. Found %: C, 51.63; H, 6.12; N, 6.04.

EXAMPLE 34

R-(−)-5-[2-[2-(5-Fluoro-2-methoxyphenoxy)-ethylamino]propyl]-2-methoxybenzenesulfonamide hydrochloride A suspension of 1.00 g of R-(−)-5-(2-aminopropyl)-2-methoxybenzenesulfonamide $[[\alpha]_D^{25} -13.8°$ (C=1,MeOH), m.p.156.5°–160.5° C. (H₂O) ] 11.00 g of 2-(2-bromoethoxy)-4-fluoroanisole and 0.20 g of potassium iodide in 40 ml of N,N-dimethylformamide was heated for 10 hours at 85° C. After cooling, the reaction mixture was poured into water, made alkaline with 10% sodium hydroxide aqueous solution and extracted with ethyl acetate. The extract was washed with water, dried and evaporated. The residue was chromatographed on silica gel using chloroform-methanol (9:1) as an eluant to give 0.81 g of the free base as colorless crystals which were recrystallized from methanol as colorless needles, m.p.144°-145° C.

Analysis for $C_{19}H_{25}FN_2O_5S$: Calculated %: C, 55.33; H, 6.11; N, 6.79. Found %: C, 55.20; H, 5.93; N, 6.54.

Specific rotation: $[\alpha]_D^{23.4} - 19.66°$ (C=1,MeOH).

The free base thus obtained was converted into the hydrochloride in a usual manner and the resulting salt was recrystallized from a mixture of ethanol and water (4:1) to give the desired compound as colorless needles, m.p.228°-230° C.

Analysis for $C_{19}H_{25}FN_2O_5S\cdot HCl$: Calculated %: C, 50.83; H, 5.84; N, 6.24. Found %: C, 50.70; H, 5.93; N, 6.26.

Specific rotation: $[\alpha]_D^{23} - 7.6°$ (C=1,MeOH).

In the usual manner, the following acid addition salts were prepared.

| | |
|---|---|
| Nitrate | m.p.183-184° C. (decomp.) (MeOH). |
| Colorless needles, | |
| Hydrobromide | m.p.223-225° C. (MeOH). |
| Colorless needles, | |
| Maleate | m.p.109-113° C. (EtOH). |
| Colorless crystals, | |
| Succinate | m.p.119-122° C. (MeOH). |
| Colorless prisms, | |
| Fumarate | m.p.162-166° C. (MeOH). |
| Colorless prisms, | |
| ½ Fumarate | m.p.191-193° C. (MeOH). |
| Colorless needles, | |

In the same manner as described in Example 34, the compound of Example 35 was prepared using S-(+)-5-(2-aminopropyl)-2-methoxybenzenesulfonamide $[[\alpha]_D^{24} + 14.7°$ (C=1,MeOH), m.p.157°-160° C.(H₂O)].

EXAMPLE 35

S-(+)-5-[2-[2-(5-Fluoro-2-methoxyphenoxy)ethylamino]propyl]-2-methoxybenzenesulfonamide hydrochloride S-(+)-5-[2-[2-(5-Fluoro-2-methoxyphenoxy)ethylamino]propyl]-2-methoxybenzenesulfonamide Colorless crystals, m.p. 138°-139° C.(EtOH).

Analysis for $C_{19}H_{25}FN_2O_5S$: Calculated %: C, 55.33; H, 6.11; N, 6.79. Found %: C, 55.24; H, 6.27; N, 6.53.

Specific rotation: $[\alpha]_D^{23.5} + 19.70°$ (C=1,MeOH).

The free base thus obtained was converted into the hydrochloride in a usual manner and the resulting salt was recrystallized from a mixture of ethanol and water (4:1) to give the desired compound as colorless needles, m.p.227.5°-230° C.

Analysis for $C_{19}H_{25}FN_2O_5S\cdot HCl$: Calculated %: C, 50.83; H, 5.84; N, 6.24. Found %: C, 50.59; H, 5.69; N, 6.36

Specification rotation $[\alpha]_D^{23} + 7.5°$ (C=1,MeOH).

EXAMPLE 36

S-(+)-5-[2-[2-(5-Fluoro-2-methoxyphenoxy)ehtylamino]propyl]-2-methoxybenzenesulfonamide L-10-camphorsulfonate A suspension of 25 g of (±)-5-[2-[2-(5-fluoro-2-methoxyphenoxy)ethylamino]propyl]-2-methoxybenzenesulfonamide and 15.2 g of L-10-camphorsulfonic acid $[[\alpha]_D^{20} - 20 \sim -23°(C=5,H_2O)]$ in 450 ml of methanol was heated to produce dissolution. The solution was allowed to cool to room temperature and the precipitate was filtered off.

The filtrate was evaporated and this procedure was repeated three times for the residue. The obtained residue was recrystallized from ethanol to give the desired compound as colorless scales, m.p.184°-184° C.

Analysis for $C_{19}H_{25}FN_2O_5S \cdot C_{10}H_{16}O_4S$: Calculated %: C, 54.02; H, 6.41; N, 4.34. Found %: C, 53.81; H, 6.15; N, 4.28

Specific rotation: $[\alpha]_D^{24} - 9.4°$ (C=1,MeOH).

To the L-10-comphorsulfonate acid salt thus obtained was added aqueous sodium hydroxide solution and the mixture was extracted with chloroform. The extract was washed with water, dried and evaporated. The residue was recrystallized from ethanol to give the free base as colorless needles which were consistent with those of Example 35.

EXAMPLE 37

R-(−)-5-[2-[2-(5-Fluoro-2-methoxyphenoxy)ethylamino]propyl]-2-methoxybenzenesulfonamide D-10-camphorsulfonate R-(−)-5-[2-[2-(5-fluoro-2-methoxyphenoxy)ethylamino]propyl]-2-methoxybenzenesulfonamide D-10-camphorsulfonate was obtained in the same manner as that described in Example 36, using (±)-5-[2-[2-(5-fluoro-2-methoxyphenoxy)ethylamino]propyl]-2-methoxybenzenesulfonamide and D-10-camphorsulfonic acid $[[\alpha]_D^{20} + 20°-23°$ (C=5,H₂O)]. The obtained crystals were consistent with those of Example 34.

EXAMPLE 38

| Tablet formulation | |
|---|---|
| Compound of Example 34 | 0.2 mg |
| Lactose | 98.8 mg |
| Magnesium Stearate | 1 mg |
| | 100 mg |

EXAMPLE 39

| Capsule formulation | |
|---|---|
| Compound of Example 1 | 0.4 mg |
| Lactose | 98.6 mg |
| Magnesium Stearate | 1 mg |
| Gelatin Capsule | |
| | 100 mg |

EXAMPLE 40

| Granule formulation | |
|---|---|
| Compound of Example 1 | 4 mg |
| D-Mannitol | 450 mg |
| Lactose | 516 mg |
| Hydroxypropylcellulose | 30 mg |
| | 1000 mg |

EXAMPLE 41

| Injection formulation | |
|---|---|
| Compound of Example 34 | 0.1 mg |
| Glucose | 100 mg |
| Distilled water for injection | a proper quantity |

-continued

| Injection formulation | |
|---|---|
| | 2 ml |

EXAMPLE 42

| Suppository formulation | |
|---|---|
| Compound of Example 1 | 1 mg |
| Hydrogenated oil | 1999 mg |
| | 2000 mg |

It is to be understood that the invention is not to be limited to the exact details of operation or exact compounds, compositions, methods, or procedures shown and described, as obvious modifications and equivalents will be apparent to one skilled in the art.

We claim:

1. A phenoxyethylamine derivative selected from those represented by the formula (I)

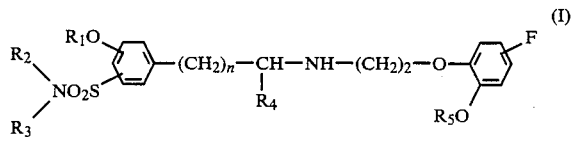

wherein $R_1$ and $R_5$ represent lower-alkyl, $R_2$ and $R_3$ may be the same or different and each represents hydrogen or lower-alkyl, or

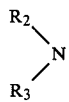

may represent the pyrrolidine radical, $R_4$ represents hydrogen or lower-alkyl, and n represents an integer selected from 1 to 3, inclusive and a pharmacologically-acceptable acid addition salt thereof.

2. Compound of claim 1 being (±)-5-[2-[2-(5-Fluoro-2-methoxyphenoxy)ethylamino]-propyl]-2-methoxybenzenesulfonamide or a pharmacologically-acceptable acid addition salt thereof.

3. Compound of claim 1 being R-(−)-5-[2-[2-(5-Fluoro -2-methoxyphenoxy)ethylamino]-propyl]-2-methoxybenzenesulfonamide or a pharmacologically-acceptable acid addition salt thereof.

4. Compound of claim 1 being 5-[2-[2-(4-Fluoro-2-methoxyphenoxy)ethylamino]-propyl]-2-methoxybenzenesulfonamide or a pharmacologically-acceptable acid addition salt thereof.

5. Compound of claim 1 being 5-[2-(2-Ethoxy-5-fluorophenoxy)ethylamino]-propyl]-2-methoxybenzenesulfonamide or a pharmacologically-acceptable acid addition salt thereof.

6. Compound of 1 being 5-[2-[2-(5-Fluoro-2-methoxyphenoxy)ethylamino]-propyl]-2-methoxy-N-methylbenzenesulfonamide or a pharmacologically-acceptable acid addition salt thereof.

7. Compound of claim 1 being 5-[2-[2-(5-Fluoro-2-methoxyphenoxy)ethylamino]-propyl]-2-methoxy-N,N-dimethylbenzenesulfonamide or a pharmacologically-acceptable acid addition salt thereof.

8. Compound of claim 1 being 5-[2-[2-(2-Ethoxy-5-fluorophenoxy)ethylamino]-propyl]-2-methoxy-N,N-dimethylbenzenesulfonamide or a pharmacologically-acceptable acid addition salt thereof.

9. Compound of claim 1 being 5-[2-[2-(5Fluoro-2-methoxyphenoxy)ethylamino]-propyl]-2-ethoxybenzenesulfonamide or a pharmacologically-acceptable acid addition salt thereof.

10. A compound of claim 1 being 1-[[5-[2-[2-(5-Fluoro-2-methoxyphenoxy)ethylamino]-propyl]-2-methoxyphenyl]sulfonyl]pyrrolidine or a pharmacologically-acceptable acid addition salt thereof.

11. Pharmaceutical composition comprising an a compound of claim 1 and a pharmaceutically-acceptable carrier or diluent.

12. A method for the treatment of hypertension or dysuria comprising the step of administering an effective amount of a compound of claim 1 or a pharmaceutical composition comprising the same, to a subject in need thereof.

* * * * *

UNITED STATES PATENT AND TRADEMARK OFFICE
CERTIFICATE OF CORRECTION

PATENT NO. : 4,971,990

DATED : Nov. 20, 1990

INVENTOR(S) : Yasuo Itoh, Hideo Kato, Eiichi Koshinaka, Nobuo Ogawa, Kazuya Mitani, Shunichiro Sakurai It is certified that error appears in the above-identified patent and that said Letters Patent is hereby corrected as shown below:

Title Page, [54] line 1 through 4; "DERIVATIVES, FOR PREPARING THE SAME AND COMPOSITION FOR EXHIBITING EXCELLENT" should read -- DERIVATIVES, PROCESS FOR PREPARING THE SAME AND COMPOSITION EXHIBITING EXCELLENT --.

Column 2, line 58; "[-2-", should read -- [2- --.
Column 3, line 1; "-2-" should read -- -[2- --. (first occurrence)
Column 3, line 48; "(5Fluoro-" should read -- (5-Fluoro- --.
Column 7, line 58; "solvents" should read -- solvent --.
Column 8, line 1; "a optical" should read -- an optical --.
Column 9, line 68; delete "as", first occurrence.
Column 10, line 10; "homogenaized" should read -- homogenized --.
Column 10, line 12; "homogenaized" should read -- homogenized --.
Column 10, line 33; "values" should read -- value --.
Column 11, line 46; "(3H,s), 3.90" should read -- (3H,s), 3.61 (2H,s), 3.90 --.
Column 13, approximate line 30; "6.32N," should read -- 6.32; N, --.
Column 14, approximate line 42; "[2(" should read -- [2-( --.
Column 15, line 34; "(1,d-" should read -- (1H,d- --.
Column 15, line 42; "[2(" should read -- [2-( --.
Column 20, approximate lines 12/13; "ethylamino]-N" should read -- ethylamino]propyl]-N --.
Column 20, Line 21/22; "ethylamino]-N" should read -- ethylamino]propyl]-N --.
Column 21, line 23; "-2methoxyphenyl" should read -- -2-methoxyphenyl --.
Column 21, line 32/33; delete "-methoxyphenyl]sulfonyl]", second occurrence
Column 21, line 34; "Cololess" should read -- Colorless --.
Column 21, line 40; "[2-[(2-" should read -- [2-[2- --.

UNITED STATES PATENT AND TRADEMARK OFFICE
CERTIFICATE OF CORRECTION

PATENT NO. : 4,971,990           Page 2 of 2

DATED : Nov. 20, 1990

INVENTOR(S) : Yasuo Itoh, Hideo Kato, Eiichi Koshinaka, Nobuo Ogawa, Kazuya Mitani, Shunichiro Sakurai It is certified that error appears in the above-identified patent and that said Letters Patent is hereby corrected as shown below:

Column 22, line 17; "50.83;" second occurrence, should read
   -- 5.84; --.
Column 22, line 41; "5-[2[" should read -- 5-[2-[ --.
Column 22, line 52; "-5-[2-(5-" should read -- -5-[2-[2-(5- --.
Column 25, approximate line 55; "Specification" should read
   -- Specific --.
Column 25, line 59/60; "ehtylamino" should read -- ethylamino --.
Column 28, line 11; "[2-(2-Ethoxy" should read
   -- [2-[2-(2-Ethoxy --.
Column 28, line 28; "5Fluoro" should read -- 5-Fluoro" --.
Column 28, line 36; delete "an". (R&A 3-7-90, P. 2)

Signed and Sealed this

Twelfth Day of May, 1992

Attest:

DOUGLAS B. COMER

Attesting Officer      Acting Commissioner of Patents and Trademarks